United States Patent [19]
Akashi et al.

[11] Patent Number: 5,945,514
[45] Date of Patent: Aug. 31, 1999

[54] ANTIVIRAL RAW MATERIALS

[75] Inventors: Mitsuru Akashi, 14-6, Koutokujidai 2-chome; Masanori Baba, 54-17, Koutokujidai 3-chome, both of Kagoshima, Kagoshima 891-01; Makoto Onishi, Kanagawa, all of Japan

[73] Assignees: Mitsuru Akashi; Masanori Baba, both of Kagoshima, Japan

[21] Appl. No.: 09/043,871

[22] PCT Filed: Jul. 18, 1997

[86] PCT No.: PCT/JP97/02501

§ 371 Date: Mar. 30, 1998

§ 102(e) Date: Mar. 30, 1998

[87] PCT Pub. No.: WO98/06266

PCT Pub. Date: Feb. 19, 1998

[30] Foreign Application Priority Data

Aug. 8, 1996 [JP] Japan .................................. 8-210323

[51] Int. Cl.⁶ .............................. C07K 1/00; C07K 14/00; A61K 38/16
[52] U.S. Cl. .................................. 530/396; 514/8; 514/54; 435/5
[58] Field of Search .................................. 530/396; 435/5; 514/8, 54

[56] References Cited

U.S. PATENT DOCUMENTS 5,462,853  10/1995  Stewart et al. ............................. 435/5

FOREIGN PATENT DOCUMENTS

| 0 214 057 | 3/1987 | European Pat. Off. ....... A61K 37/02 |
| 61-165334 | 7/1986 | Japan ............................. A61K 37/46 |
| 08319300 | 12/1996 | Japan ............................. C07K 17/10 |
| 9806266 | 2/1998 | WIPO ............................. A01N 63/02 |

*Primary Examiner*—Avis M. Davenport
*Attorney, Agent, or Firm*—Sughrue, Mion, Zinn, Macpeak & Seas, PLLC

[57] ABSTRACT

The present invention relates to an antiviral raw material having mannose-binding type lectin bound, through a hydrophilic high-molecular chain, to a base material composed of a hydrophobic high-molecular chain. The raw material has excellent shape stability and at the same time has excellent antiviral activity so that it can be used in a wide range of fields.

3 Claims, No Drawings

ANTIVIRAL RAW MATERIALS

TECHNICAL FIELD

The present invention relates to a raw material which captures or inactivates a virus, thereby expressing antiviral activity.

BACKGROUND ART OF THE INVENTION

In recent days, various diseases attributable to a virus have come to be a serious social problem. It is known, for example, that diseases such as AIDS, viral hepatitis type B, viral hepatitis type C and adult T-cell leukemia are caused by HIV, HBV, HCV and HTLV-I, respectively. Furthermore, appearance of new viral diseases such as Ebola hemorrhagic fever and Marburg disease caused by Filovirus and hemorrhagic fever with renal syndrome caused by Hantaan virus has posed a great threat to humans.

As one of the important countermeasures for the prevention of the diseases attributable to a virus, infection prevention can be given. In various fields ranging from the production sites of blood derivatives or vaccines, hospitals and bio-related research institutes to our daily life, countermeasures against infection with a virus are being requested. As a technique for the removal or inactivation of a virus, a heat treatment method is well known, but it is difficult to carry out heat treatment in some cases, for example, where a biological component which is degenerated or deactivated by the heat treatment is contained or where the object to be treated is an organism itself.

Known examples of the non heat-treating method include:

(1) a method of inactivating a virus by using a virus inactivating agent;

(2) a method of making a virus adsorb to a material having a target cell of the virus or a receptor immobilized thereto, thereby removing the virus (U.S. Pat. No. 4869826); and (3) a method of capturing a virus in water by using polyvinyl pyridinium beads which have been insolubilized by crosslinking (Japanese Patent Publication No. SHO 62-41641).

The above-described method (1) however involves problems in the safety of a chemical used for the inactivation of a virus, separation of the chemical from the treatment solution contained in the inactivated virus and degeneration of useful proteins in the treatment solution. As a method of inactivating a virus by using a chemical, an inactivation method with a surfactant, aldehyde or β-propiolactone has already been reported. It is however known that the inactivating method of a virus by using such a chemical degenerates or impairs physiological activity of a protein component. According to the report, β-propiolactone remains in the treatment solution even after inactivation of a virus and exhibits carcinogenicity, so that it has not yet come into wide use. Also proposed is a method of removing a virus by treating the virus with a liposoluble virus inactivating agent and then distributing said virus inactivating agent in a natural oil or synthetic triglyceride of less toxicity (Japanese Patent Application Laid-Open No. SHO 62-240623). This method is however accompanied with the drawback that it requires cumbersome and long-time operation.

The above-described method (2) is not satisfactory from the viewpoints of adjustment of a material, stability (maintenance of activity) and economy because a cell itself or its receptor is employed as the material. In addition, it is accompanied with the drawback that owing to high specificity to a target virus, it cannot be applied to many non-specific viruses.

By the above-described method (3) which uses a polyvinyl pyridinium structure, a virus can be captured and removed from tap water or the like having a small protein content. From the plasma or a cellular culture solution which contains proteins and lipids at high concentrations, on the other hand, a virus cannot be removed effectively because nonspecific adsorption of protein components and lipids mainly occurs.

Accordingly, an object of the present invention is to provide an antiviral raw material which has overcome the above-described problems. More specifically, an object of the present invention is to provide a virus-infection preventive which is, for the purpose of preventing the infection of a virus, applied in advance to the mucous tissue, thereby inhibiting the invasion of a virus; or a virucide which can safely and conveniently remove or inactivate a virus existing in a solution or the air.

DISCLOSURE OF THE PRESENT INVENTION

With a view to finding an antiviral raw material which has overcome the above-described problems, the present inventor has carried out an extensive investigation. As a result, it has been found that a raw material which has excellent form stability and strength and effectively expresses antiviral activity of lectin can be obtained by binding a mannose binding type lectin to a hydrophobic base material through a hydrophilic high-molecular chain, leading to the completion of the present invention.

BEST MODES FOR CARRYING OUT THE INVENTION

The antiviral raw material according to the present invention features that a hydrophilic high-molecular chain having mannose-binding type lectin bonded thereto is bonded to a base material composed of a hydrophobic high-molecular chain. Examples of the preferred form of the antiviral raw material includes fine particles.

The term "lectin" means a generic name of sugar-binding type proteins and it is known to manifest activities such as agglutination of cells, induction of division, functional activation, functional suppression and cytopathy by being bonded to a sugar chain of a conjugated polysaccharide of a cell membrane.

No particular limitation is imposed on the mannose-binding type lectin to be used in the present invention insofar as it is a lectin which can recognize a mannosyl residue in a polysaccharide or conjugated polysaccharide. Examples of a lectin capable of recognizing an α-mannosyl residue which is a component sugar of the base nucleus of an asparagine-binding sugar chain include Conavalia ensiformis (concanavalin A; Con A), Lens culinaris (LCA), Bowringia midbraedii (BMA), Dolichos lablab (DLA), Galanthus nivalis (GNA), Gerardiasavaglia (GSL), Machaerium biovulatum (MBA), Machaeriumu lunatus (MLA), Narcissus pseudonarcissus (NPA), Epipactis heleborine (EHA) and Listera ovata (LOA). Among the above-described mannose-binding type lectins, Con A is particularly suited from the viewpoints of function and economy.

In the present invention, mannose-binding type lectin is designed to manifest its function by acting on the high mannose region of membrane glycoprotein on the surface layer of a virus. It is desired to determine the raw material according to the using purpose or application, because the degree of antiviral activity differs with the kind of lectin or virus.

As a total structure of the base material to be bound with a mannose-binding type lectin in the present invention, it is desired that a hydrophilic high-molecular chain and a hydrophobic high-molecular chain are formed as a block or graft copolymer and particularly, the hydrophilic high-molecular chain exists as a graft chain of the hydrophobic high-molecular chain. The use of the hydrophobic high-molecular chain as the base material makes it possible to provide an antiviral raw material having improved strength and size stability in water and having excellent performance and operability. In addition, the hydrophilic high-molecular chain used as a graft chain covers the surface layer portion of the base material composed of the hydrophobic high-molecular chain, suppresses the adsorption of nonspecific proteins owing to hydrophobic interaction in an aqueous solvent, thereby providing an environment permitting the easy manifestation of selective adsorption of lectin. In the case where the base material takes the form of fine particles, the hydrophilic high-molecular chain existing on the surface enables uniform dispersion in the aqueous solvent.

No particular limitation is imposed on the structure of the hydrophobic high-molecular chain used in the present invention. It is however preferred that the hydrophobic high-molecular chain is composed of a water-insoluble high molecule having a water absorption ratio less than 2%, because water absorption ratios not less than 2% deteriorate the strength or size stability of the material in water or decrease the particle size of the fine particles, thereby increasing the surface area and making it difficult to increase an amount of lectin to be held.

For example, a hydrophobic high-molecular chain selected from acrylate esters, methacrylate esters, polymers or copolymers of styrene or its derivative, polyolefins, polysulfones, polyamides, polyesters, polyurethanes and polyimides. Copolymers of such a hydrophobic high-molecular chain may also be usable.

No particular limitation is imposed on the structure of the hydrophilic high-molecular chain to be used in the present invention. However, a polymer which is soluble or has an absorption ratio not less than 2% in an aqueous solution and has a recurring structure formed of monomers is preferred, because nonspecific adsorption due to hydrophobic interaction or agglutination between fine particles tend to occur at water absorption ratios less than 23%.

As the hydrophilic high-molecular chain, usable are polymers or copolymers each of which contains, as a component, acrylamide or methacrylamide or a derivative thereof; a monomer, such as acrylic acid or methacrylic acid, having in its molecule a carboxyl group; a monomer, such as vinylsulfuric acid or styrenesulfonic acid, having in its molecule a sulfuric acid group; a monomer, such as vinylamine or allylamine, having in its molecule an amine; N-vinylacetamide or an N-vinylalkylamide; vinylpyrrolidone or vinylpyrrolidinone; a vinyl ether; a hydrophilic monomer having an amino acid or sugar in its molecule; an aziridine compound; a monomer having phospholipid in its molecule; or an acrylate ester or methacrylate ester and corresponds to a hydrophilic high molecule. Any one of polyether compounds, polysaccharides, polyamides, polyesters and polyurethanes can also be used insofar as it has a water absorption ratio not less than 2%.

Preferred examples of the hydrophilic high-molecular chain include water-soluble high-molecular chains, such as acrylamide, derivatives thereof and N-vinylacetamides, which can suppress the nonspecific adsorption of proteins.

High-molecular chains, such as quaternary ammonium salts, having a strong basic ion exchange group; and hydrophobic high-molecules such as polypropylene and polyethylene are not preferred because they heighten the nonspecific protein adsorption, thereby lowering lectin-induced antiviral action.

In the present invention, examples of the usable method for binding a mannose-binding type lectin to a hydrophilic high molecule include, first as a covalent bonding method, the cyanogen bromide activation method through an imidocarbonato derivative, condensation reagent method using a carbodiimide reagent or Woodward reagent, diazo method through a diazonium compound, acid azide derivative method, halogenated acetyl derivative method, triazinyl derivative method, halogenated methacrylic (acrylic) acid derivative method and crosslinking method using a polyfunctional crosslinking agent such as glutaraldehyde or both-terminal epoxy compound.

Such a binding method is employed because lectin is considered to have a functional group such as carboxyl, amino, hydroxyl, imidazole or phenol so that a functional group, such as diazonium salt, acid azide, isocyanate, halogenated alkyl, epoxy or aldehyde, which reacts with the above functional group may be introduced into a hydrophilic high-molecular chain or may be reacted with lectin under the suitable conditions by using a crosslinking agent or condensing agent.

In order to introduce a functional group into a hydrophilic high-molecular chain, copolymerization of a monomer having said functional group, conversion from a monomer having another functional group, or the like can be employed.

As a method other than the covalent bonding method, an ion exchange group or lectin binding site is introduced into a hydrophilic high-molecular chain, thereby carrying out non-covalent bonding immobilization by making use of electrostatic interaction or specific affinity.

Incidentally, when sustained release of lectin is not aimed at, immobilization by the covalent bonding method is preferred.

A description will next be made of the using form of the antiviral raw material according to the present invention.

The antiviral raw material according to the present invention is preferred to take the form of fine particles, because various types of preparations or materials having antiviral effects can be designed using such a raw material. For example, by dispersing a fine-particulate antiviral raw material in a liquid, it becomes possible to design a wide variety of preparations including not only an aerosol preparation used by spraying to a membrane tissue, which is an infection route, for preventing the infection with a virus, but also a semi-solid preparation such as ointment or cream and a solid preparation. In addition, an antiviral raw material in the form of fine particles can be used by being filled into a column or by being blended with a molding or forming raw material or a surface treatment agent.

Examples of the method to obtain the fine-particulate material include a method making use of mechanical pulverization or abrasion, a method of precipitating fine particles during the synthesizing step of high molecules and a method of forming fine particles by insolubilizing or cooling and solidifying the material in the form of a solution or under molten state.

Examples of the process for the preparation of fine particles composed of a hydrophilic high-molecular chain for binding of lectin and a hydrophobic high-molecular chain which is a main component of the base material include:

(1) a method of forming anti-viral fine particles by forming fine particles of a hydrophobic high-molecular chain to be a base material and then binding or grafting a hydrophilic high-molecular chain on the surface of the resulting base material;

(2) a method of forming anti-viral fine particles by preparing hydrophobic fine particles using a monomer or macromonomer having a functional group convertible, by hydrolysis or the like, from a hydrophobic group to a hydrophilic group; and then converting the hydrophobic fine particles into a hydrophilic high-molecular chain by making use of hydrolysis or the like; and (3) a method of forming anti-viral fine particles by using hydrophilic and hydrophobic raw materials in combination, for example, using a hydrophilic macromonomer and a hydrophobic monomer or a hydrophobic macromonomer and a hydrophilic monomer in combination.

Among the above-exemplified methods, a method of forming anti-viral fine particles during the synthesizing step of a high molecule is preferred from the viewpoints of uniformity of fine particles and easiness in preparation.

For example, when a hydrophilic macromonomer is subjected to dispersion copolymerization with a hydrophobic monomer such as styrene or butyl methyl methacrylate in water, ethanol or a mixed solvent of ethanol and water, high-molecular microspheres which are called microspheres or nanospheres, have a relatively uniform particle size and exhibit good dispersibility in water can be synthesized (Mitsuru Akashi, "Water-soluble Macromonomer", High-molecular Processing, 37, 120–125, which is incorporated herein by reference). The use of this method makes it possible to conveniently and uniformly prepare fine particles which have a hydrophilic high molecule as a nucleus and have a surface covered with a hydrophilic high molecular chain. The fine particles available by this method has excellent strength and stability (size change due to swelling is small) so that it is suited as a base material (carrier) for immobilizing lectin.

The term "macromonomer" means a polymer having a function as a polymerizable monomer. The macromonomer is formed by the synthesis of a main chain polymer and introduction of a polymerizable functional group. Examples of the method include a method making use of the chain transfer reaction in anionic living polymerization (termination method, initiation method), cationic polymerization (ring-opening cationic living polymerization, vinyl cationic polymerization, cationic polymerization making use of initiator) or radical polymerization; and a method of introducing a polymerizable functional group to a functional group such as that at the terminal of the main chain polymer by using chloromethylstyrene, glycidyl methacrylate, methacryloyl isocyanate, methacrolein, methacrylic acid chloride or the like (Ryuzo Asami, "Synthesis and Polymerization of Macromer", High-molecular Processing, 33, 439–445, which is incorporated herein by reference).

The preferred fine particle size of the antiviral raw material according to the present invention ranges from 100 nm to 1 mm. The particle size must be decreased in order to widen the surface area of the fine particles per unit volume. When the particle size is not greater than 100 nm, it approaches the size of a virus, which diminishes its effects on separation or inactivation. Particle sizes exceeding 1 mm, on the other hand, lower the adsorption rate and efficiency, thereby impairing practical utility.

The present invention applies to every virus for which mannose-binding type lectin exhibits inactivating effects and as one of the useful and important target viruses, there exists a causative virus (HIV) of AIDS which has recently become a social problem. Mannose-binding type lectin such as Con A is bound to a sugar chain of gp120, which is an envelope glycoprotein of HIV, and manifests anti-HIV activity. The lectin is therefore expected to exhibit effects for the removal of infectious HIV particles from a treated solution or a body fluid and prevention of infection; or for the removal of gp120, which is regarded as a substance causing a disease in the organism, or an antigen-antibody complex thereof.

The antiviral raw material according to the present invention can be used for everything that requires antiviral activity.

Examples of the material to which the antiviral raw material of the present invention can be applied include pharmaceuticals or various products (various products for medical use, nursing or daily use) used for preventing secondary infection from a virus carrier; raw materials or additives for medical tools or clinical examination articles used in a medical site or clinical examination site where viral infection presumably occurs; treatment apparatuses for reducing a virus load of infected patients; and virus concentrating apparatuses used in an examination or test.

Specific examples include an antiviral agent for the preliminary administration to a route to be infected with a virus in order to prevent the viral infection; an antiviral medicament for inactivating a virus in a biological sample used for clinical examination or the like, or a medical container having the medicament filled therein; an ointment or cream applied to the skin or the like in order to prevent the viral infection, and a medical tool for inactivating HIV or removing gp120 from the body of the patients infected with HIV in order to reduce a virus load.

It is particularly necessary to provide an inexpensive and convenient prophylactic for AIDS for the purpose of inhibiting the expansion of its infection. Infection with HIV upon sexual intercourse or the like can be prevented by processing the antiviral raw material according to the present invention into a spraying agent, a solid preparation, a semi-solid preparation or the like and then administering it to an infection route such as vagina.

Accordingly, the antiviral raw material according to the present invention is a raw material for lowering the risk of viral infection (preventing the viral infection) or improving the morbid condition attributable to a virus by adsorbing or inactivating all or some of virus particles. It can be used not only as fine particles for capturing or inactivating a virus but also an additive for imparting a forming or molding raw material or surface treatment agent with antiviral activity, a prophylactic against the infection to organisms (humans, vegetables, animals, fishes and shellfishes), an additive to a medical tool or treatment tool or a component itself.

EXAMPLES

The present invention will next be described more specifically by examples. It should however be borne in mind that the present invention is not limited to or by the following examples.

Example 1 and-Comparative Examples 1 to 3

(1) Synthesis of fine particles having a hydrophilic high-molecular chain

In tetrahydrofuran, t-butyl methacrylate (t-BMA) was dissolved. The resulting solution was polymerized at 60° C. for 6 hours in a nitrogen gas stream in the presence of a chain transfer agent (2-mercaptoethanol) and a polymerization initiator (azobisisobutylonitrile; AIBN). After the completion of the reaction, the reaction mixture was re-precipitated in a mixed solution of water and methanol (1/1, v/v), dried under reduced pressure and dissolved in isopropanol. The resulting solution was re-precipitated in a mixed solution of water and methanol again, whereby a t-BMA oligomer having at a terminal thereof a hydroxyl group was obtained [Refer to M. Riza, S. Tokura, M. Iwasaki, E. Yashima, A. Kishida, M. Akashi, J. Polym. Sci. Part A: Polym. Chem. Ed., 33, 1219–1225 (1995), which is incorporated herein by reference].

The t-BMA oligomer so obtained was dissolved in 100 ml of DMF (N,N-dimethylformamide), followed by the addition of 5 times the molar equivalent of a phase transfer catalyst (tetrabutylphosphonium bromide) and 10 times the molar equivalent of a 50% aqueous KOH solution based on the oligomer. After stirring at 30° C. for 60 minutes, the reaction mixture was added with 10 times the molar equivalent of p-chloromethylstyrene and they were reacted by stirring at 30° C. for 48 hours. After the completion of the reaction, the reaction product was re-precipitated in a mixed solution of water and methanol (1/1, v/v), dried under reduced pressure and then dissolved again in isopropanol. The resulting solution was re-precipitated in a mixed solution of water and methanol again, whereby a t-BMA macromonomer having at a terminal thereof a vinylbenzyl group was obtained. The molecular weight of the macromonomer can be controlled by synthesis conditions, however, a macromonomer having a molecular weight (Mn) of 2,000 to 10,000 is ordinarily used.

In a deaerated and sealed tube, the resulting t-BMA macromonomer and styrene were reacted at 60° C. for 48 hours in ethanol in the presence of AIBN as an initiator. The reaction product was then purified by dialysis in methanol and dried under reduced pressure, whereby fine particles (which will hereinafter be called "microspheres") were obtained. The resulting microspheres were thereafter dispersed in ethanol. To the dispersion, concentrated hydrochloric acid (ethanol/hydrochloric acid; 5/1, v/v) was added and the resulting mixture was reacted at 75° C. for 12 hours, whereby the t-BMA chain was converted into a methacrylic acid chain. Subsequent to the removal of the supernatant and concentration, purification was effected by dialysis with water.

By the above-described operation, microspheres having polymethacrylic acid as a hydrophilic high-molecular chain and polystyrene as a hydrophobic high-molecular chain were obtained.

The size of the microspheres can be controlled by the monomer composition or synthesis conditions and those having a size ranging from 100 nm to 1000 nm are preferably used. In this example, the following test was carried out using microspheres having a particle size of 200 nm to 400 nm.

(2) Immobilization of the mannose-binding type lectin

An immobilizing method will next be described with concanavalin A (Con A), which is mannose-binding type lectin, as an example.

To 1.2 ml of a dispersion (250 mg/ml) of the microspheres (M1) obtained above, 0.15 ml of a 0.5M $KH_2PO_4$ solution and 0.15 ml of a 1.0 wt. % aqueous solution of WSC (1-ethyl-3-(dimethylaminopropyl)carbodiimide hydrochloride) were added. The resulting mixture was allowed to stand at room temperature for 30 minutes, whereby the carboxyl group on the surface of the microspheres was activated. By centrifugal separation at 13,000 rpm for 20 minutes, the microspheres were separated from the solution. Immediately after the removal of the solution portion (supernatant), a 1.0 mg/ml Con A solution (10 mM HEPES buffer, pH 8.0, 4° C.) was added to the residue. The resulting mixture was allowed to stand at 4° C. for 24 hours, whereby Con A was immobilized to the microspheres. After the completion of the reaction, centrifugal separation (at 13,000 rpm for 20 minutes) and re-dispersion were repeated, whereby an unreacted portion of Con A was removed.

The amount of Con A immobilized on the surface of the microspheres was determined from a calibration curve which had been made in advance in a Con A solution by the color development of an amino acid formed by hydrolysis in 2N-HCl at 100° C. for 2 hours. The immobilized amount of Con A on the surface can be controlled by the structure of the microspheres or reaction conditions, but in the following test, anti-HIV action was measured using the microspheres having Con A immobilized in an amount of 2 mg/cm$^2$.

(3) Measurement of anti-HIV action

With HIV, which is a virus causing AIDS, as a target, anti-HIV action of Con A-immobilized microspheres was evaluated.

The HIV virus stock solution was prepared by culturing MOLT-4/HIV, which is an HTLV-III$_3$ persistent infectious cell, in a 10% FCS-containing RPMI 1640 medium and then subjecting the resulting cultured solution to centrifugal separation to separate therefrom cellular components. The virus stock solution so obtained was adjusted to an HIV solution having a predetermined infectious value by adding a 10% FCS-containing RPMI 1640 medium prior to use. The HIV infectious value was calculated as the tissue culture infectious dose 5% (TCID 50/ml) by measuring cytopathic effects (CPE) on MT-4 cells in accordance with the conventional method. The amount of gp120 which is an envelope glycoprotein of HIV, on the other hand, was determined using "gp120 Capture ELIZA kit" produced by AGMED Inc.

Each of the substances shown in Table 1 was mixed with an equivalent amount of an HIV-I virus solution. The resulting mixture was incubated at room temperature for 60 minutes, followed by centrifugation at 4° C. and 1,500 g for 10 minutes. An amount of gp120 antigen contained in the supernatant and infections value were determined. Incidentally, microspheres in Comparative Example 1 have a surface not immobilized with Con A, while those in Comparative Example 2 are added, but not immobilized, with Con A and its concentration is similar to the concentration of Con A existing freely as an inclusion in a microsphere floating solution.

TABLE 1

| | Substance added | Amount of gp 120 antigen (ng/ml) | Infectious value (x10$^4$ TCID 50/ml) |
|---|---|---|---|
| Ex. 1 | Con A immobilized microspheres | 0.015 ± 0.011 | 2.3 ± 1.4 |
| Comp. Ex. 1 | Microspheres | 4.36 ± 0.48 | 6.9 ± 1.1 |
| Comp. Ex. 2 | Con A (0.79 mg/ml) | 3.73 ± 0.16 | 7.9 ± 3.6 |
| Comp. Ex. 3 | Control solution (10 mM HEPES) | 4.99 ± 0.68 | 9.8 ± 3.9 |

It has been found that the Con-A immobilized microspheres in Example 1 captured gp120, which is membrane glycoprotein deeply participating in the infection of HIV to host cells, at an efficiency as high as 90% or higher. It has also been found that compared with the control solution, the infectious value of the Con-A immobilized microspheres was reduced by about 70%.

INDUSTRIAL APPLICABILITY

Since the antiviral raw material according to the present invention has mannose-binding type lectin bonded, through a hydrophilic high-molecular chain, to a base material composed of a hydrophobic high-molecular chain, it has excellent shape stability and strength and exhibits antiviral activity of lectin effectively.

By preparing the antiviral raw material of the present invention in the form of fine particles having a diameter of 100 nm to 1 mm, a variety of formulations or materials can be designed. For example, it becomes possible to design a wide variety of formulations including not only an aerosol preparation used by spraying to a membrane tissue or the like to prevent viral infection but also semi-solid preparations such as ointment or cream and solid preparations. It also becomes possible to add it to a molding or forming material or surface treatment agent prior to processing into a desired shape; or to impart the molded or formed product with antiviral action.

Japanese Patent Application No. 8-210323 filed Aug. 8, 1996 is incorporated herein by reference in its entirety.

We claim:

1. An antiviral raw material, which comprises mannose-binding type lectin bonded, through a hydrophilic high-molecular chain, to a base material composed of a hydrophobic high-molecular chain.

2. An antiviral raw material according to claim 1, wherein said hydrophilic high-molecular chain has a water absorption ratio of 2% or higher and said hydrophobic high-molecular chain has a water absorption ratio less than 2%.

3. An antiviral raw material according to claim 1 or 2, which is in the form of fine particles having a diameter of 100 nm to 1 mm.

* * * * *